United States Patent [19]

Cocker et al.

[11] Patent Number: 5,480,523
[45] Date of Patent: Jan. 2, 1996

[54] METHOD OF USING OXYGEN MEASURING PROBE

[75] Inventors: Alan J. Cocker, Ormskirk; Esther C. Batchelor, Burscough, both of United Kingdom

[73] Assignee: Pilkington plc, United Kingdom

[21] Appl. No.: 357,788

[22] Filed: Dec. 16, 1994

Related U.S. Application Data

[63] Continuation of Ser. No. 35,786, Mar. 23, 1993, abandoned.

[30] Foreign Application Priority Data

Mar. 24, 1992 [GB] United Kingdom .................. 9206367

[51] Int. Cl.$^6$ ................................................. G01N 27/411
[52] U.S. Cl. .................... 204/153.18; 65/99.2; 65/99.4; 204/422; 204/424
[58] Field of Search ...................... 204/153.18, 421–429; 65/99.2–99.6

[56] References Cited

U.S. PATENT DOCUMENTS

| | | | |
|---|---|---|---|
| 3,464,008 | 8/1969 | Meysson et al. ........................ | 204/422 |
| 3,468,780 | 9/1969 | Fischer .................................... | 204/422 |
| 3,578,578 | 5/1971 | Von Krusenstierna ................. | 204/422 |
| 3,616,407 | 10/1971 | Engell et al. ........................... | 204/423 |
| 3,619,381 | 11/1971 | Fitterer .................................... | 204/423 |
| 3,625,026 | 12/1971 | Cocker .................................... | 65/99.4 |
| 3,773,641 | 11/1973 | Fitterer .................................... | 204/423 |
| 3,791,954 | 2/1974 | Noda ....................................... | 204/423 |
| 3,841,987 | 10/1974 | Friese et al. ............................ | 204/427 |
| 4,003,814 | 1/1977 | Tarassoff et al. ....................... | 204/422 |
| 4,177,125 | 12/1979 | Barnabe .................................. | 204/424 |
| 4,178,222 | 12/1979 | Murphy et al. ......................... | 204/427 |
| 4,230,555 | 10/1980 | Sano et al. .............................. | 204/427 |
| 4,251,342 | 2/1981 | Habdas et al. .......................... | 204/427 |
| 4,310,402 | 1/1982 | Isenberg et al. ........................ | 204/424 |
| 4,313,799 | 2/1982 | Perkins ................................... | 204/153.18 |
| 4,366,039 | 12/1982 | Uchida et al. .......................... | 204/153.18 |
| 4,547,281 | 10/1985 | Wang et al. ............................. | 204/153.18 |
| 4,944,861 | 7/1990 | Reber ...................................... | 204/421 |

FOREIGN PATENT DOCUMENTS

| | | |
|---|---|---|
| 2118666 | 7/1972 | France . |
| 2578981 | 9/1986 | France . |
| 3811864 | 10/1989 | Germany . |
| 1271747 | 4/1972 | United Kingdom . |
| 1283712 | 8/1972 | United Kingdom . |
| 1347937 | 2/1974 | United Kingdom . |
| 1372732 | 11/1974 | United Kingdom . |
| 1381976 | 1/1975 | United Kingdom . |
| 1398835 | 6/1975 | United Kingdom . |
| 1569524 | 6/1980 | United Kingdom . |

*Primary Examiner*—T. Tung
*Attorney, Agent, or Firm*—Howrey & Simon

[57] ABSTRACT

An oxygen measuring probe for use with molten metal baths for the manufacture of glass which probe comprises a probe body (4) comprising an elongate tubular member (6) closed at one end by a separate tip part (8) formed of stabilised zirconia which constitutes a solid electrolyte through which oxygen ions can pass, said tubular member (6) being formed of a heat-resistant material different from said zirconia, a first electrode (16) connected to the inner surface of the zirconia tip part (8), earthing means adapted for connection to earth out of contact with the molten metal and voltage measuring means (24) connected between the first electrode (16) and said earthing means (26).

3 Claims, 2 Drawing Sheets

METHOD OF USING OXYGEN MEASURING PROBE

This application is a continuation of application Ser. No. 08/035,786, filed on Mar. 23, 1993, now abandoned.

FIELD OF THE INVENTION

The present invention relates to an oxygen measuring probe for use with molten metal baths for the manufacture of glass, and to a method of use of such a probe.

BACKGROUND OF THE INVENTION

In the float glass process in which a bath of molten tin or tin alloy is used to support an advancing ribbon of glass, oxygen is a major contaminant. Oxygen is believed to be responsible directly or indirectly for reducing glass quality in several ways, giving rise to poor bloom grades, CO bubble, tin speck faults and for tin pick-up faults.

In the float glass process the bath atmosphere is controlled, generally by maintaining an atmosphere of nitrogen and hydrogen. In practical terms it is impossible to exclude oxygen completely from the bath; oxygen can enter the bath by various pathways, such as through the exit seal, through leaks in windows and side seals, as a contaminant of the atmosphere supply, or with the glass itself as dissolved oxides (e.g. $SO_2$ and $H_2O$). A series of interactions then take place with hydrogen in the atmosphere, with the tin, and with the glass itself. It is not economic to attempt to reduce the contamination below a particular level. Ingress can, however, be reduced to a level at which its deleterious effects are of little or no consequence.

It is clearly important to know the amount of oxygen present so that if this rises, appropriate steps can be taken to prevent further contamination, whilst the glass subject to contamination and the level of contamination can be readily identified.

The oxygen content of the tin can be measured by conventional analytical techniques; by removing a sample, reacting with carbon under vacuum and measuring the carbon monoxide released. This is however a lengthy procedure which demands great skill and care if the required degree of precision is to be achieved; as a result, this measurement is rarely performed.

The chemical state of the bath with respect to oxygen contamination can also be monitored on a regular basis using indirect means such as an atmosphere extractive technique, measurement of the tin count, or measurement of the bloom grade. The extractive technique indicates the level of contamination of the atmosphere but does not necessarily say anything about the level of contamination in the tin. Further, being an extractive technique, the sample lines are prone to blockage. The tin count and bloom grade are measurements made on the glass, and are indicative of the amount of tin present in the surface, which is directly related to the level of oxygen contamination. Since these tests are carried out on the product there is necessarily a time delay and the results give little indication of the distribution of contamination within the bath.

A known technique for measuring the oxygen content of the molten tin on an in situ basis uses a measuring probe located in the bath so as to extend into the molten tin. This probe is the subject of U.S. Pat. No. 3,625,026. The probe comprises a tubular body of zirconia which has been doped to induce conductivity to oxygen ions and which thereby constitutes a solid electrolyte. Electrical connection is made to the inside of the tube, and directly to the molten tin which as a conductor constitutes an electrical connection to the outside of the tube. A galvanic cell is thereby effectively set up, resulting from the oxygen concentration internally of the tube which is separated from the oxygen concentration in the molten tin by the solid zirconia electrolyte. The cell emf is indicative of the oxygen concentration at the outer side of the probe. By supplying a gas of constant oxygen concentration to the inside of the tube an absolute value for the oxygen concentration externally of the tube can be determined.

Various problems exist with this probe. The probe body of zirconia is particularly fragile, and is sensitive to thermal shock arising on insertion of the probe into the molten tin, which may typically be at 700° C. Zirconia has a high thermal coefficient of expansion, such that on this initial insertion, considerable stresses are set up within the zirconia body, rendering the probe liable to fracture. There is a further thermal effect which arises on more prolonged usage which can cause the probe to fracture. The stabilisation of the zirconia by the addition of dopants causes the zirconia to take a particular crystalline form (specifically, a cubic tetragonal form). Although this form is stable at the temperature of the molten tin, at lower temperatures, below about 400° C., the stable form of zirconia is a different crystalline form (specifically, a cubic monoclinic form), and on prolonged usage a transition to this form will occur. A substantial temperature gradient exists along the length of the probe when in use, such that the temperature conditions in which the second crystalline form is the stable form are generally found at a region of the probe remote from the molten tin. This change of crystalline structure involves a volume change, such that a junction region between the two forms of zirconia will constitute a particular site of stress at which the zirconia body is liable to fracture.

SUMMARY OF THE INVENTION

The present invention seeks to provide an oxygen measuring probe which overcomes these problems.

In order to derive an accurate measurement of the oxygen concentration, in addition to obtaining a value for the cell emf, one requires a value for the cell temperature. Such a value can be obtained from separately measuring the molten metal temperature. It has also been proposed to measure the probe temperature with a thermocouple extending part way within the probe. Neither of these means ensure accurate temperature measurement of the cell.

According to one aspect of the invention there is provided a oxygen measuring probe for use with molten metal baths for the manufacture of glass, which probe comprises: a tubular probe body comprising an elongate tubular member closed by a separate tip part which is connected thereto, which tip part is formed of stabilised zirconia which constitutes a solid electrolyte through which oxygen ions can pass, said tubular member being formed of a heat resistant material different from said zirconia; and an emf measuring device for measuring the emf generated in use between inner and outer surfaces of the zirconia tip part, wherein a thermocouple disposed in contact with an inner surface of the zirconia tip part is provided for measuring the temperature of the zirconia tip part.

By providing a thermocouple which is in contact with the zirconia tip part one obtains a direct measurement of the actual cell temperature. By providing only a tip part of zirconia this will rapidly reach in its entirety the high temperature in or above the bath of molten metal, and so the risk of failure due to thermal shock is reduced. Furthermore, when the probe is inserted in the molten metal with the entire tip part immersed, the entire tip part will be held at a temperature above that at which a change of crystalline form could occur.

A further advantage arising from the probe structure of the invention is that prior to assembly, the inside surface of the zirconia tip part can be easily accessed. The unitary zirconia body of the known probe is very long and thin such that access to the inside of the tip is very difficult, and it is therefore very difficult to form a good electrical connection of the electrode to the inner surface of the tip.

A further difficulty which arises is that it is problematic to secure the electrode to the inner surface of the zirconia tip part, and where a thermocouple is additionally provided this problem also applies to the thermocouple wires. Preferably, the emf measuring device, and the thermocouple include a common electrode in the form of a metallic wire connected to an inner surface of the zirconia tip part, the thermocouple further comprising an additional thermocouple wire of different composition connected to the first electrode at the tip part to form a thermocouple junction therewith.

Preferably, with the present probe the first electrode wire and the additional thermocouple wire are connected to the inner surface of the zirconia tip part by means of a cement of platinum applied as a paste. This gives a particularly secure and effective electrical and thermal contact with the zirconia tip part. The common electrode may be formed of platinum, and the additional thermocouple wire formed of a platinum alloy.

In an embodiment adapted specifically for measuring the oxygen concentration in the atmosphere above the tin bath, the emf measuring device comprises a first electrode connected to an inner surface of the zirconia tip part, a second electrode connected to the outer surface of the tip part, and a voltmeter connected between the first and second electrodes. In this case both first and second electrodes are secured to the tip part by means of a cement of platinum applied as a paste.

A further problem encountered with the known probe arises from the fact an electrical connection must be made directly into the molten tin. Connection has previously been made by a platinum wire having a length of rhenium wire welded to the end of this platinum wire, with only the rhenium extending into the molten tin. Rhenium is used because, unlike platinum, it is not attacked by the molten tin, and is relatively stable towards oxygen at the concentrations which generally exist in float glass baths. However, if a severe oxygen contamination occurs, the rhenium can become oxidised, whereby the electrical connection is disrupted.

According to a further aspect of the present invention there is provided an oxygen measuring probe for use with molten metal baths for the manufacture of glass, which probe comprises an elongate tubular body closed at a measuring end thereof for insertion into the molten metal, at least a portion of the body at the measuring end being formed of stabilised zirconia, which constitutes a solid electrolyte through which oxygen ions can pass, a first electrode connected to an inner surface of the zirconia portion, earthing means adapted for connection to earth out of contact with the molten metal, and voltage measuring means connected to the first electrode and to said earthing means.

With this arrangement there is no reliance on direct electrical connection to the molten metal. The arrangement uses the observation that the molten metal is effectively an earth, so that measurement of the emf between the probe electrode and a direct connection to earth is effectively equivalent to measurement between the probe electrode and molten metal which is in contact with an outer side of the zirconia, subject to correction of any emf's arising from junctions in the electrical connections earth. This modification also simplifies construction and reduces the cost of the probe.

The tubular probe body preferably comprises an elongate tubular member which is closed at the measuring end by a separate tip part of stabilised zirconia, sealed to the tubular member, said tubular member being formed of a heat-resistant material which is different from said zirconia.

Preferably, the elongate tubular member is formed of alumina, and the zirconia tip part is sealed to the alumina tube by a glass ceramic material having a thermal expansion coefficient intermediate between that of alumina and zirconia. The use of a glass ceramic material of matched thermal expansion provides an effective non-porous seal, which is able to absorb to some extent the thermal expansion of the zirconia tip on initial insertion into or location adjacent to the molten metal.

Preferably, the zirconia tip part comprises a generally annular portion received within an end of the tubular member, at which the tip part is sealed to the elongate tubular member, and a hollow relatively short outwardly convex portion depending therefrom. Conveniently the outwardly convex portion may be of substantially conical shape, the connection of the first electrode being made within the tip part in the region of the apex thereof. The shortness and internal shape of the zirconia tip part facilitites appropriate location of the platinum paste and electrode on assembly of the probe.

The probe preferably also includes means for direction of an oxygen-containing reference gas onto the inner surface of the zirconia tip part. Maintaining a known concentration of oxygen within the probe tip is essential where an absolute value for oxygen concentration on the outside of the probe tip is required.

The invention in a further aspect also resides in a method of measuring the oxygen concentration in molten metal with a probe as defined hereinabove, wherein the probe is inserted into the molten metal and said earthing means are connected to earth out of contact with the molten metal.

BRIEF DESCRIPTION OF THE DRAWINGS

Embodiments of the present invention are described, by way of example only, with reference to the following drawings in which.

DESCRIPTION OF THE PREFERRED EMBODIMENTS

Figure 1:
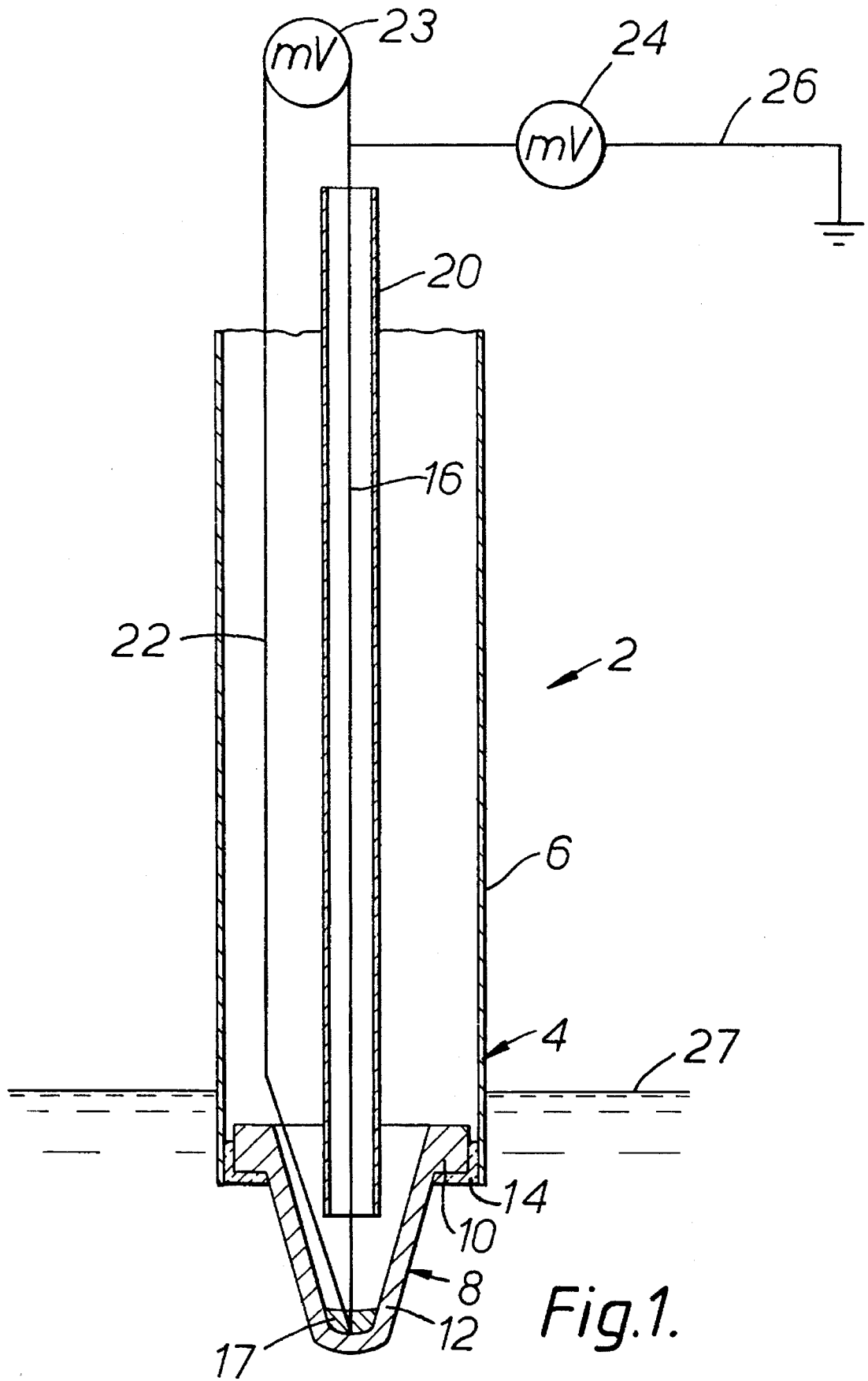
FIG. 1 is a schematic view of a first embodiment of a measuring probe in accordance with the invention, adapted for measuring the oxygen concentration in molten tin.

Turning to FIG. 1 of the drawings, a first embodiment of an oxygen measuring probe 2 is shown, the probe comprising a tubular probe body 4 closed at one end which constitutes a measuring end, which in use is immersed in a bath of molten tin of a float glass bath. The probe body 4 comprises a cylindrical tubular member 6 formed of a heat-resistant refractory material, such as alumina, which is closed at its lower end by a tip part 8 formed of zirconia (zirconium oxide). The zirconia is stabilised by the addition of one or more of CaO, MgO and $Y_2O_3$ as is known in the art, whereby the zirconia constitutes a solid electrolyte which allows conduction of oxygen ions therethrough. The zirconia tip part 8 comprises an annular portion 10 at which the tip part 8 is attached to the tubular part 6, and a hollow generally conical portion 12 depending therefrom.

The tip part 8 is connected to the tubular member 6 by means of a glass ceramic material 14 which forms a non-porous seal therebetween. The glass ceramic material is arranged to have a coefficient of thermal expansion intermediate between that of zirconia and alumina. This matched expansion glass ceramic seal is formed according to the method of Rogers, Butler and Steele as disclosed in *J. Sci. Inst.* (*J. Physics E*) 1969 Ser. 2 volume 2 page 102, although in the present case the seal is formed between alumina and zirconia, instead of between a alumina and metal as in the reference.

A reference electrode 16 comprises a wire, formed preferably of platinum, extending within the probe body 4 along the length thereof, which is electrically and thermally connected to the inner surface of the tip part 8 at the inner apex thereof.

A particularly effective connection can be obtained by cementing the electrode to the zirconia tip by means of a platinum paste, indicated at 17. The paste comprises a suspension of platinum in a viscous organic medium which is applied to the inside of the tip part with the electrode embedded therein, and then fired to volatilise the organic medium, leaving the electrode cemented to the tip part.

It is intended that on assembly of the probe, the connection of the platinum wire electrode 16 is made to the tip part 8 prior to the connection of the tip part 8 to the tubular member 6, since easy access is then possible.

An internal annular tube 20 of refractory material, preferably alumina, surrounds the electrode wire 16. This internal tube 20 forms a passageway for the supply of a reference gas containing a known amount of oxygen, typically air, to the inner surface of the tip part 8. Maintenance of a known oxygen concentration at the inner surface of the tip is necessary where it is required to calculate an absolute value for oxygen concentration in the molten tin, as is apparent from the calculations shown below. It is also highly desirable to maintain a constant oxygen concentration internally where only relative changes of emf are used to indicate relative change of oxygen concentration in the bath. The tube 20 also serves to protect the platinum electrode 16 from the effects of heat.

A further wire 22 extends within the probe body 4 and is connected to the electrode wire 16 where this is cemented to the tip part 8, to form a thermocouple junction with the electrode wire 16. Thus, the electrode wire 16 forms a common electrode wire for both the voltage measurement and temperature measurement. This simplifies the design and assembly. The wire 22 is preferably formed of a platinum alloy, for example a 13% Rh/Pt alloy. A millivoltmeter 23 provided externally of the probe body 4 is connected between the wire 16 and wire 22; measurement of the thermoelectric emf developed between the electrode wire 16 and wire 22 enables a value for the temperature at the tip to be obtained, which temperature value is necessary for a calculation of an absolute value for oxygen concentration in the molten tin. Tube 20, electrode 16 and thermocouple wire 22 are supported in fixed positions at an upper end of the probe housing 4 within a sleeve member (not shown).

Also externally of the probe body 4, the reference electrode 16 is connected to a millivoltmeter 24 which is in turn connected to a measuring electrode 26. This measuring electrode 26 is in turn connected to earth. Typically, a metal portion of the bath casing or unpainted water pipe provides the earth. The electrode 26 may, but need not, be of platinum. In practice the platinum of electrode 16 may terminate at the probe head and have a lead to the meters of a different material, the electrode 26 also being of that different material. Use of the same electrode material for the electrodes on both sides of the millivoltmeter obviates the need for correction of the measurement of emf resulting from the electrode/millivoltmeter junction; however, a correction to the measured emf is required as a result of an emf generated by the junction of the measuring electrode 26 and earth return. The millivoltmeter is a high impedance millivoltmeter, for example of input impedance $10^{13}$ ohms, whereby polarisation of the cell is avoided.

In use, the probe is positioned with the tip part 8 entirely immersed in the molten tin. The tin level is indicated in FIG. 1 by reference numeral 27. The entire tip part 8 therefore remains at a temperature above that at which a change of crystalline form could occur. The region where the temperature conditions exist which would cause the change of crystalline form in zirconia are found at the part of the probe formed of alumina, in which no such change occurs and so presents no thermal stress problem. Furthermore, the surface of the molten tin, which also constitutes a site of thermal stress, lies in the region of the alumina tubular member 6, which material is considerably less susceptible to thermal stress-induced fracture than zirconia. Air is directed at the inner surface of the tip part 8 via the tube 20, and measurements taken of the emf shown by the voltmeter 24, which emf is indicative of the oxygen concentration in the molten tin.

The relationship between the measured emf and oxygen concentration in the molten tin is derivable as follows:

Oxygen reacts with tin according to the equation:

$$_{1/2}Sn_{liq} + {_{1/2}}O_2 \text{ gas} \leftrightarrows {_{1/2}}(SnO_2) \text{ solution}$$

By Mass Action Law:

$$K = \frac{a(O)_{Sn}}{a\,Sn^{1/2} \times P_{O_2}^{1/2}}$$

thus $$P_{O_2}^{1/2} = \frac{a(O)_{Sn}}{K \times a\,Sn^{1/2}}$$

where
$K$ = Equilibrium constant
$a\,Sn$ = Activity of tin, taken as 1
$a(O)_{Sn}$ = Activity of Oxygen in tin from thermodynamic tables:

$$K = \frac{15317}{T} - 5.63$$

where $T$ = absolute temperature

The activity of oxygen in tin is defined as follows:

$$a(O)Sn = \frac{\text{Concentration of Oxygen in tin}}{\text{Saturated Concentration of Oxygen in Tin}} = \frac{C}{C_s}$$

The saturated concentration of oxygen in tin is given in the reference "Thermodynamics and Solubility of oxygen in liquid metals Part 2—Tin, T. N. Belford and C. B. Alcock TFS 61,443 (1965)" as:

$$C_s \text{ (ppm)} = 1.345 \times 10 \cdot \left( \frac{-5730 + 4.19}{T} \right)$$

Thus we can relate the oxygen partial pressure over a solution of oxygen in tin to the oxygen concentration as follows:

$$\log P_{O_2} = 2\log C_S - 3.378 - \frac{19174}{T}$$

The Nernst equation relates this partial pressure to the Emf as follows:

$$E = \frac{RT}{4F} \ln \frac{(P_{O_2} \text{ reference})}{P_{O_2}}$$

If
$E$ = Emf developed in millivolts
$R$ = Universal gas constant
$F$ = Faraday constant
Reference Gas = Air
$P_{O_2}$ reference = 0.21 atmospheres
then Oxygen concentration $(C_s)$ =                         Equation 1

$$10 \cdot \left( \frac{0.9512 + 1.339 \times 10^{-4} \times T - E \times 10^{-3}}{9.922 \times 10^{-5} \times T} \right)$$

The above relation ignores any error which exists as a result of an emf generated by the platinum wire 26/earth return couple. Where only changes in oxygen concentration in the tin are required to be measured, it is not necessary to correct for this thermoelectric emf. However, this may be done readily by modifying the constant appropriately:

The thermoelectric emf generated by the platinum wire/earth return couple (E') may be represented by the equation:

$$E' = 0.01025 \times T - 6.45$$

then, the emf E in equation 1 above is replaced by (E+ E').

Figure 2:
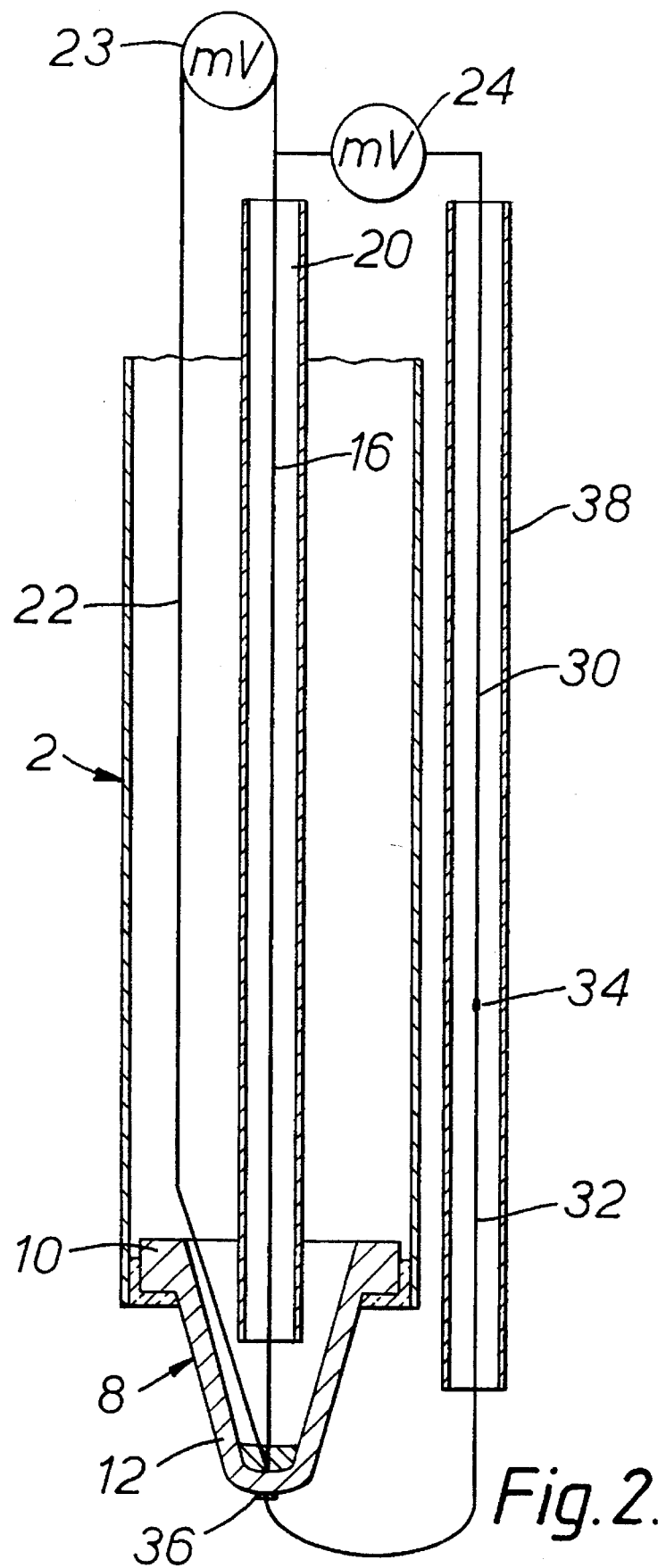
FIG. 2 is a schematic view of a second embodiment of a measuring probe in accordance with the invention, adapted for measuring the oxygen concentration in the atmosphere above a bath of molten tin.

A modification of the measuring probe of FIG. 1 allows the measurement of oxygen concentration in the atmosphere above the tin bath. This modified probe is shown in FIG. 2, in which like numerals are used to indicate like parts. In this case, since the zirconia tip part 8 which constitutes the solid electrolyte is not immersed in the molten tin, electrical connection to the outer surface of the tip must be provided; the measurement of the emf generated by the cell requires direct measurement of the potential at the inner and outer surfaces of the zirconia tip part 8. This connection is preferably in the form of a platinum wire 30 which is connected to the millivoltmeter 24 and to a length of rhenium wire 32 at a welded joint 34. The rhenium wire 32 is cemented by platinum paste at 36 to the outer surface the zirconia tip part 8, opposite the internal connection of the electrode 16, in the manner as described above in relation to the connection of the electrode 16. A further alumina tube 38 is used to enclose the platinum wire 30 and upper portion of the rhenium wire 32 to protect these from the atmosphere.

In this case, the Nernst equation can be used to relate the emf developed to the oxygen concentration in the atmosphere as follows:

$$E = \frac{RT}{nF} \ln \frac{(P_{O_2} \text{ reference})}{P_{O_2}}$$

If
$E$ = Emf developed by probe in millivolts
$R$ = Universal gas constant
$F$ = Faraday constant
$T$ = Absolute temperature
Reference Gas = Air
$P_{O_2}$ reference = 0.21 atmospheres
then $$P_{O_2} \text{ (atm)} = 0.21 \times 10 \cdot \frac{(-E \times 20.16)}{T}$$

Here, since the bath atmosphere contains hydrogen, the platinum cement on the outer surface of the probe tip 8 catalyses a reaction between hydrogen and oxygen, and the voltage generated by the measuring probe will relate not to free oxygen, but to that which would be present at equilibrium.

What we claim is:

1. In the manufacture of glass using a bath of molten metal, a method of measuring the oxygen concentration in said both with an elongate tubular member closed by a separate tip part formed of stabilized zirconia which constitutes a solid electrolyte, which tubular member is formed of a different material from zirconia, the zirconia tip part comprising a generally annular portion received within an end of the tubular member, at which the tip part is sealed to the elongate tubular member, and a hollow portion depending therefrom having inwardly sloping walls which meet to define an apex at an end of the zirconia tip part remote from the tubular member, to whereby define a substantially conically shaped portion and wherein a thermocouple is disposed in said substantially conically shaped portion of the tip part and is in contact with an inner surface thereof for measuring the temperature of the zirconia tip part, said thermocouple being located between said inwardly sloping walls and in contact with the inner surface of the tip part at the apex, said method comprising inserting the probe into the molten metal until the zirconia tip part is fully immersed therein, measuring the temperature of the apex with said thermocouple, and measuring the voltage between the inner and outer surfaces of the zirconia tip part as oxygen ions pass through the solid zirconia electrolyte.

2. A method of measuring the oxygen concentration in a molten metal as claimed in claim 1, wherein said probe further comprises a first electrode connected to the inner surface of the conically shaped portion, and said method further comprising the steps of connecting earthing means to earth out of contact with the molten metal and measuring the voltage generated between the first electrode and the earthing means as oxygen ions pass through the solid zirconia electrolyte, the molten metal acting as an earth whereby the measured voltage represents the voltage generated across the solid electrolyte.

3. In the manufacture of glass using a float glass process in which a bath of molten metal is used to support an advancing ribbon of glass, a method of limiting the oxygen contamination of the molten metal float bath, said method comprising steps of monitoring the oxygen concentration in the molten metal by inserting a probe into said molten metal bath, said probe having a tubular probe body comprising an elongate tubular member closed by a separate tip part which is connected thereto, which tip part is formed of stabilized zirconia which constitutes a solid electrolyte through which oxygen ions can pass, said tubular member being formed of a heat resistant material different from said zirconia; and an emf measuring device for measuring the emf generated in use between inner and outer surfaces of the zirconia tip part, the zirconia tip part comprising a generally annular portion received within an end of the tubular member, at which the tip part is sealed to the elongate tubular member, and a hollow portion depending therefrom having inwardly sloping walls which meet to define an epex at an end of the zirconia tip part remote from the tubular member, to thereby define a substantially conically shaped portion and wherein a thermocouple is disposed in said substantially conically shaped portion of the tip part and is in contact with an inner surface thereof for measuring the temperature of the zirconia tip part, said thermocouple being located between said inwardly sloping walls and in contact with the inner surface of the tip part at the apex, the method further comprising measuring the temperature of the apex with said thermocouple, measuring the voltage between the inner and outer surfaces of the zirconia tip part as oxygen ions pass through the solid zirconia electrolyte and preventing further oxygen contamination if an excessive oxygen concentration is indicated by the probe.

* * * * *